United States Patent
Tang

(10) Patent No.: US 10,722,228 B2
(45) Date of Patent: Jul. 28, 2020

(54) SUTURE ANCHORS HAVING LOCATION PLACEMENT IDENTIFICATION FEATURES

(71) Applicant: Medos International Sàrl, Le Locle (CH)

(72) Inventor: Howard Tang, Raynham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 652 days.

(21) Appl. No.: 15/042,893

(22) Filed: Feb. 12, 2016

(65) Prior Publication Data

US 2017/0231615 A1    Aug. 17, 2017

(51) Int. Cl.
*A61B 17/04* (2006.01)
*A61B 90/00* (2016.01)

(52) U.S. Cl.
CPC .. *A61B 17/0401* (2013.01); *A61B 2017/0403* (2013.01); *A61B 2017/0412* (2013.01); *A61B 2017/0414* (2013.01); *A61B 2090/036* (2016.02); *A61B 2090/0807* (2016.02)

(58) Field of Classification Search
CPC ........ A61B 17/0401; A61B 2017/0403; A61B 2017/0412; A61B 2017/0414; A61B 2017/0445; A61B 2017/0446; A61B 2017/0459
See application file for complete search history.

(56) References Cited

U.S. PATENT DOCUMENTS

| | | |
|---|---|---|
| 4,034,850 A | 7/1977 | Mandel et al. |
| 4,164,046 A | 8/1979 | Cooley |
| 4,549,545 A | 10/1985 | Levy |
| 5,156,056 A | 10/1992 | Pittman et al. |
| 5,245,081 A | 9/1993 | Hauptreif et al. |
| 5,258,016 A | 11/1993 | Dipoto et al. |
| 5,383,904 A | 1/1995 | Totakura et al. |
| 5,733,307 A | 3/1998 | Dinsdale |
| 6,508,830 B2 | 1/2003 | Steiner |
| 6,814,741 B2 | 11/2004 | Bowman et al. |
| 7,218,972 B2 | 5/2007 | Rodriguez |
| 7,329,272 B2 | 2/2008 | Burkhart et al. |

(Continued)

OTHER PUBLICATIONS

Merriam-Webster defintion for "alignment" as accessed Sep. 3, 2019; https://www.merriam-webster.com/dictionary/alignment.*

*Primary Examiner* — Wade Miles

(57) ABSTRACT

Devices and methods are provided for identifying a location of a bore in bone when inserting a suture anchor into bone. One exemplary embodiment of a suture anchor includes an elongate cylindrical body having a proximal terminal end surface, a distal terminal end surface, a lumen extending from the proximal terminal end surface to the distal terminal end surface, at least one bone engaging feature formed on an outer surface of the body, and a bore identification feature incorporated as part of the body. In some instances, the bore identification feature results from opposed sides of an outer surface having disparate lengths, with the side having the longer length serving as the bore identification feature. In other instances, the bore identification feature includes a protrusion that extends from, or is part of, the distal terminal end surface. Other exemplary embodiments, as well as methods for identifying a bore in bone, are also provided.

25 Claims, 5 Drawing Sheets

(56) References Cited

U.S. PATENT DOCUMENTS

| | | | |
|---|---|---|---|
| D587,807 S | 3/2009 | Wolf et al. | |
| 7,678,134 B2 | 3/2010 | Schmieding et al. | |
| 7,833,244 B2 | 11/2010 | Cerundolo | |
| 7,892,256 B2 | 2/2011 | Grafton et al. | |
| 8,083,769 B2 | 12/2011 | Cauldwell et al. | |
| 8,133,258 B2 | 3/2012 | Foerster et al. | |
| 8,298,262 B2 | 10/2012 | Stone et al. | |
| 8,361,113 B2 | 1/2013 | Stone et al. | |
| 8,409,251 B2 | 4/2013 | Cooper et al. | |
| 8,460,340 B2 | 6/2013 | Sojka et al. | |
| 8,506,596 B2 | 8/2013 | Stone et al. | |
| 8,545,535 B2 | 10/2013 | Hirotsuka et al. | |
| 8,740,913 B2 | 6/2014 | Schneider | |
| 8,790,368 B2 | 7/2014 | Sullivan et al. | |
| 8,845,685 B2 | 9/2014 | Stone et al. | |
| 2002/0111653 A1* | 8/2002 | Foerster | A61B 17/0401 606/232 |
| 2007/0034669 A1 | 2/2007 | de la Torre et al. | |
| 2009/0306711 A1* | 12/2009 | Stone | A61B 17/0401 606/232 |
| 2010/0016869 A1 | 1/2010 | Paulk et al. | |
| 2010/0179591 A1 | 7/2010 | Saltzman et al. | |
| 2010/0249700 A1 | 9/2010 | Spivey | |
| 2010/0249805 A1 | 9/2010 | Olson et al. | |
| 2011/0087267 A1 | 4/2011 | Spivey et al. | |
| 2012/0053623 A1* | 3/2012 | Sojka | A61B 17/0401 606/232 |
| 2012/0071959 A1 | 3/2012 | Helgesson | |
| 2013/0023928 A1 | 1/2013 | Dreyfuss | |
| 2013/0103081 A1 | 4/2013 | Wolf | |
| 2013/0144334 A1 | 6/2013 | Bouduban et al. | |
| 2013/0158599 A1 | 6/2013 | Hester et al. | |
| 2013/0345750 A1 | 12/2013 | Sullivan | |
| 2014/0107701 A1 | 4/2014 | Lizardi et al. | |
| 2014/0222038 A1 | 8/2014 | Seedhom et al. | |
| 2014/0257385 A1 | 9/2014 | Lunn et al. | |
| 2015/0025552 A1 | 1/2015 | Stoll | |
| 2015/0066079 A1 | 3/2015 | Schmieding | |
| 2016/0022288 A1 | 1/2016 | Bouduban et al. | |

\* cited by examiner

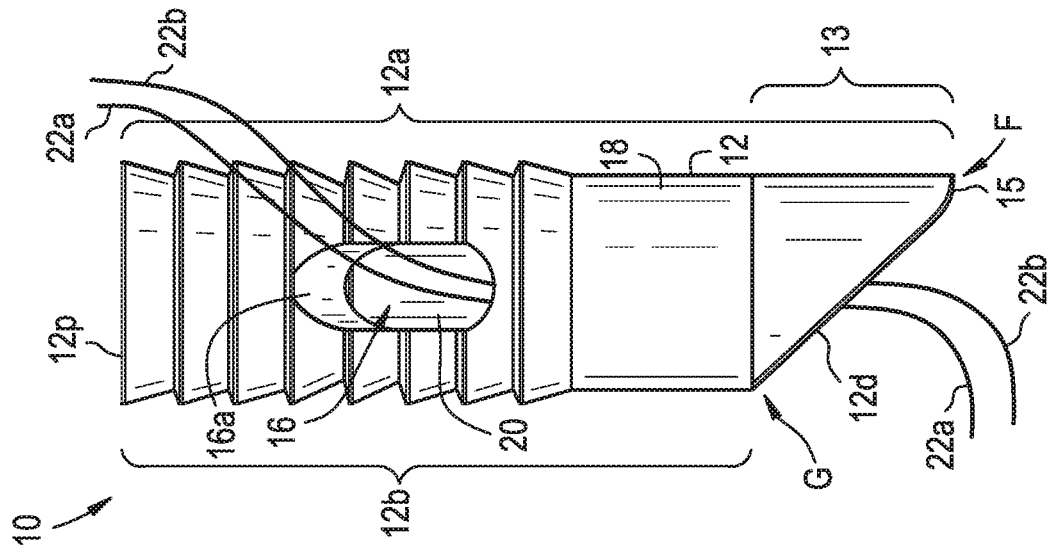
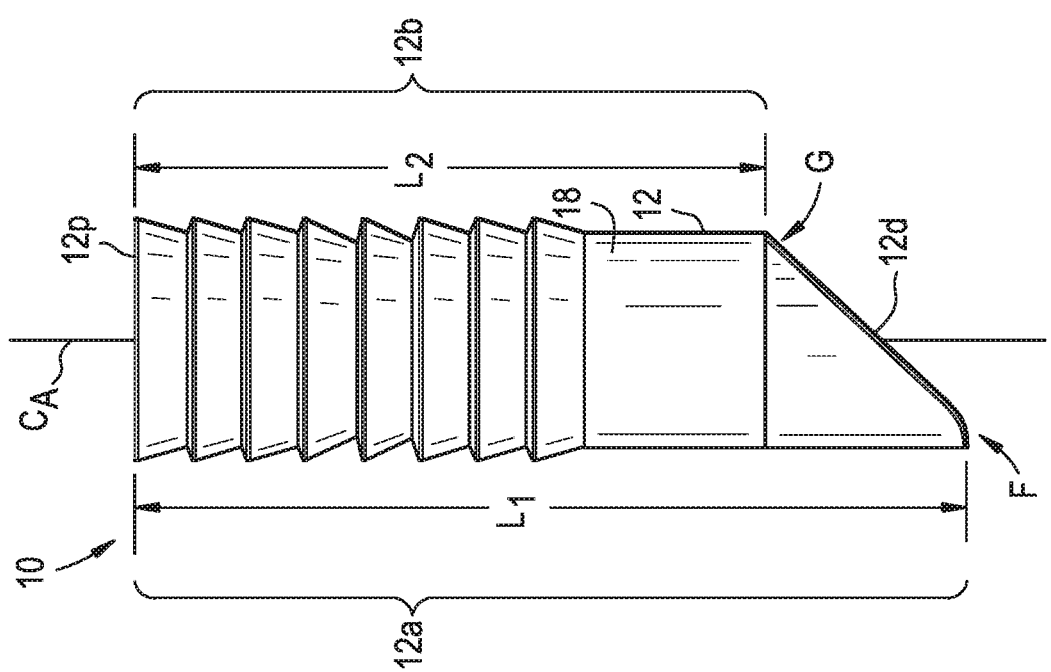

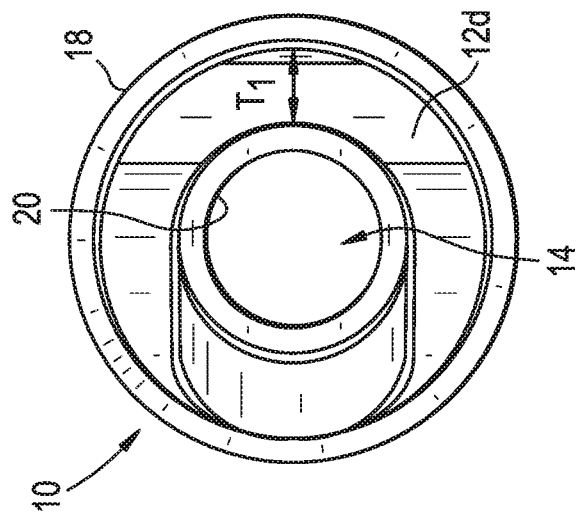
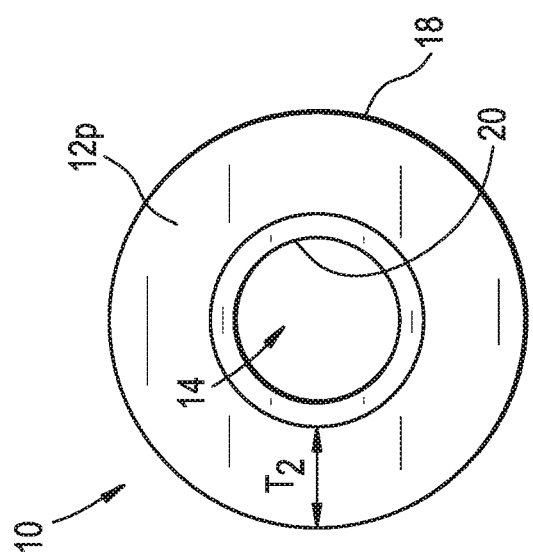

SUTURE ANCHORS HAVING LOCATION PLACEMENT IDENTIFICATION FEATURES

FIELD

The present disclosure relates to devices and methods for identifying and guiding the surgical device to a desired location and orientation with respect to a bone, and more particularly relates to the use of an identification feature disposed at a distal end of a suture anchor.

BACKGROUND

Many surgical procedures involve placing an implant into bone. In some instances, the implant is driven directly into the bone, while in other instances, a bone hole is pre-formed in the hole and the implant is secured within the pre-formed hole. The implant can have a variety of configurations, but a common implant used for soft tissue repair is a suture anchor in combination with a suture. The anchor is disposed in the bone, and the suture or filament is coupled to the anchor, engages the tissue, and is tied or otherwise secured to maintain a location of the tissue with respect to the bone in which the anchor is implanted. In some exemplary procedures, the anchor and related suture can be configured such that a surgeon does not need to tie any knots during the course of the procedure.

One particularly complex anatomy for inserting a suture bone anchor is the shoulder joint, for example, during a glenoid labrum fixation procedure. During traditional glenoid labrum fixation procedures, one or more bone anchors are inserted into the bone through cartilage adjacent to the glenoid rim. The glenoid rim can be small, difficult to access, and can have an irregular surface, making it difficult for surgeons to insert an anchor into the glenoid rim at a location that is far enough away from the edge to prevent the implant from overly damaging the bone. Although this procedure has been traditionally performed through open surgical techniques, recently there has been a shift to provide for a minimally invasive form of glenoid labrum fixation, which further complicates correct placement of the knotless suture bone anchor on the glenoid fossa.

Moreover, typically knotless suture bone anchors require that a suture be passed through or otherwise coupled to the anchor prior to fixing the anchor in the bone. In some such instances, a guide wire or other such guide device can be used to help align the anchor being implanted into a desired location in the bone. The additional instrumentation can consume more space at or near the surgical site, create more potential points of failure, and can increase the amount of time a procedure takes by virtue of having to operate more instrumentation. Furthermore, in some embodiments, a surgeon may install the anchor without the use of a K-wire or other such device to direct the anchor to a drill bore in the bone, for instance because the tool is difficult to use in a small surgical area or is otherwise unavailable to the surgeon for a particular type of procedure. Thus, during a minimally invasive glenoid fixation procedure, for example, poor visibility can result in situations where it becomes hard to find a pre-formed bore in the bone for installing the suture anchor.

Present knotless suture bone anchors can be difficult to use in procedures with poor visibility at the surgical site. In some instances, it can take one minute or longer just to locate a bore into which an anchor is to be implanted, and in some extreme instances the bone hole may not be found, and thus a new hole is formed. Further, due to the relatively small size of the bone hole and the bone anchor, it is often difficult to insert the anchor, even when visibility is not an issue. This is particularly the case when using knotless anchors in which the suture is advanced ahead of the anchor, and thus, the suture may become sandwiched between the distal end of the anchor and the bone. This can result in lower resolution feedback from the distal end of the anchor sliding across the bone, referred to as "soft" feedback, and can make finding the drill hole even more difficult because it will be harder to feel any differences in the surface features, e.g., the bore, of the bone.

It is therefore desirable to provide devices and methods for use in soft tissue repair that allow for an implant location to be easily identified by a surgeon so the device can be easily inserted to the proper location even when the surgeon's visibility during the procedure is poor, while also avoiding suture entanglement during the repair procedure.

SUMMARY

Devices and methods are generally provided for securing soft tissue to bone. The devices and methods can also be adapted for use in securing one or more objects, such as bone fragments or tissue, and for drawing two or more tissues together so they can be secured in a desired location, among other surgical procedures. In one exemplary embodiment a suture anchor includes an elongate cylindrical body having a proximal terminal end surface, a distal terminal end surface, a lumen extending from the distal terminal end surface, towards the proximal terminal end surface, and to an opening formed in the elongate cylindrical body, and at least one bone engaging feature formed on an outer surface of the elongate cylindrical body. The distal terminal end surface surrounds the lumen formed in the surface. A first portion of the distal terminal end surface disposed on one side of the lumen projects further away from the proximal terminal end surface than a second portion of the distal terminal end surface disposed on a second, opposed side of the lumen projects from the proximal terminal end surface. As a result, the first portion is configured to locate a bone hole for implantation of the suture anchor.

In some embodiments the opening of the suture anchor can be formed in a side of the elongate cylindrical body such that a portion of the lumen extends from the outer surface to an inner wall that defines another portion of the lumen. In such embodiments, a center of the opening can be located approximately 90 degrees around a circumference of the outer surface of the elongate cylindrical body from a side of the body that includes the distal-most portion of the first portion. Alternatively, a center of the opening can be located approximately along a side of the elongate cylindrical body that includes the distal-most portion of the first portion. Still further, in some embodiments, a surface of the elongate cylindrical body that defines the opening can include a chamfer formed along a proximal end of the surface. In some embodiments, the lumen can extend through the body from the distal terminal end surface to the proximal terminal end surface.

At least one bone engaging feature can include, for example, a plurality of ribs formed along a proximal portion of the outer surface. The distal terminal end surface can be substantially cylindrical in shape, and a thickness of the first portion of the distal terminal end surface can be greater than a thickness of the second portion of the distal terminal end surface. In such embodiments, the first portion of the distal terminal end surface can include a substantially flat shoulder. The first portion can project at least about 0.5 millimeters further away from the proximal terminal end surface than the second portion projects away from the proximal terminal end surface.

In some embodiments, the suture anchor can include a cylindrical wedge having a distal-most surface that defines the first portion of the distal terminal end surface of the cylindrical body. A thickness of a proximal-most portion of the cylindrical wedge can be equal to or less than a thickness of the cylindrical body extending between the outer surface and an inner wall of the cylindrical body that defines the lumen. In such embodiments, the distal terminal end surface of the cylindrical body that is not included as part of the cylindrical wedge can be substantially flat and can form a substantially uniform length between the distal terminal end surface and the proximal terminal end surface.

Another exemplary embodiment of a suture anchor includes an elongate cylindrical body having a proximal terminal end surface, a distal terminal end surface, a lumen extending from the distal terminal end surface, towards the proximal terminal end surface, and to an opening formed in the elongate cylindrical body, and at least one bone engaging feature formed on an outer surface of the elongate cylindrical body. The suture anchor has disparate lengths measured along opposed sides of the outer surface of the elongate cylindrical body, with the length on both sides being defined as the distance between the proximal terminal end surface and the distal terminal end surface of the body. The disparate lengths can be, for example, a first length of the suture anchor being greater than a second length of the suture anchor. By way of non-limiting example, in some embodiments, a difference between the first length and the second length can be approximately at least about 0.5 millimeters.

In some embodiments the opening of the suture anchor can be formed in a side of the elongate cylindrical body such that a portion of the lumen extends from the outer surface to an inner wall that defines another portion of the lumen. In such embodiments, a center of the opening can be located approximately 90 degrees around a circumference of the outer surface of the elongate cylindrical body from the first length. Alternatively, a center of the opening can be located approximately along the first length. Still further, in some embodiments, a surface of the elongate cylindrical body that defines the opening can include a chamfer formed along a proximal end of the surface. In some embodiments, the lumen can extend through the body from the distal terminal end surface to the proximal terminal end surface.

At least one bone engaging feature can include, for example, a plurality of ribs formed along a proximal portion of the outer surface. The distal terminal end surface can be substantially cylindrical in shape, and a thickness of the distal terminal end surface at the first length can be greater than a thickness of the distal terminal end surface at the second length. In such embodiments, a portion of the distal terminal end surface that encompasses the first length can include a substantially flat shoulder.

In some embodiments, the suture anchor can include a cylindrical wedge having a distal-most surface that defines a portion of the distal terminal end surface of the cylindrical body. A thickness of a proximal-most portion of the cylindrical wedge can be equal to or less than a thickness of the cylindrical body extending between the outer surface and an inner wall of the cylindrical body that defines the lumen. In such embodiments, the distal terminal end surface of the cylindrical body that is not included as part of the cylindrical wedge can be substantially flat and can form a substantially uniform length between the distal terminal end surface and the proximal terminal end surface.

Still another exemplary embodiment of a suture anchor includes an elongate cylindrical body having a proximal terminal end surface, a distal terminal end surface, a lumen extending from the distal terminal end surface, towards the proximal terminal end surface, and to an opening formed in the elongate cylindrical body, and at least one bone engaging feature formed on an outer surface of the elongate cylindrical body. The distal terminal end surface has a first portion that extends further away from the proximal terminal end surface along a first longitudinal axis of the elongate cylindrical body than a second portion of the distal terminal end surface extends away from the proximal terminal end surface along a second longitudinal axis that is parallel to the first longitudinal axis. Further, the first and second portions of the distal terminal end surface are on opposed sides of the outer surface of the elongate cylindrical body.

In some embodiments the opening is formed in a side of the elongate cylindrical body such that a portion of the lumen extends from the outer surface to an inner wall that defines another portion of the lumen. In such embodiments, a center of the opening can located approximately 90 degrees around a circumference of the outer surface of the elongate cylindrical body from the first portion. Still further, in some embodiments, a center of the opening can be located approximately along a longitudinal axis extending between the proximal end surface and the first portion. A surface of the elongate cylindrical body that defines the opening can include a chamfer formed along a proximal end of the surface. In some embodiments, the lumen can extend through the body from the distal terminal end surface to the proximal terminal end surface.

At least one bone engaging feature can include, for example, a plurality of ribs formed along a proximal portion of the outer surface. The distal terminal end surface can be substantially cylindrical in shape, and a thickness of the distal terminal end surface at the first portion can be greater than a thickness of the distal terminal end surface at the second portion. In such embodiments, the first portion can include a substantially flat shoulder.

An amount the first portion of the distal terminal end surface extends further away from the proximal terminal end surface along the first longitudinal axis of the elongate cylindrical body can be approximately at least about 0.5 millimeters greater than an amount the second portion of the distal terminal end surface extends away from the proximal terminal end surface along the second longitudinal axis. In some embodiments, the suture anchor can include a cylindrical wedge having a distal-most surface that defines a portion of the distal terminal end surface of the cylindrical body. A thickness of a proximal-most portion of the cylindrical wedge can be equal to or less than a thickness of the cylindrical body extending between an inner wall of the cylindrical body that defines the lumen and the outer surface. The distal terminal end surface of the cylindrical body that is not included as part of the cylindrical wedge can be substantially flat and can form a substantially uniform length between the distal terminal end surface and the proximal terminal end surface.

In one exemplary embodiment of a surgical method of affixing tissue to bone includes passing a suture through tissue, coupling the suture to a suture anchor, and positioning a bore identification feature of a distal-most surface of the anchor in a bore formed in a bone. The method further includes manipulating the suture anchor to position the suture anchor in the bore, securing the suture anchor within the bore; and manipulating the suture to secure a location of the tissue with respect to the bone.

In some embodiments the bore identification feature can extend distally beyond a proximal-most portion of a distal terminal end surface of the suture anchor. For example, the bore identification feature can extend approximately at least about 0.5 millimeters distally beyond the proximal-most portion of the distal terminal end surface of the suture anchor. The suture anchor can be brought towards and positioned in the bore formed in the bone without assistance from a guidance surgical instrument. In some embodiments, the method can further include drilling the bore formed in the bone. The step of manipulating the suture anchor to position the suture anchor in the bore can further include applying tension to the suture. The step of coupling the suture to a suture anchor can further include passing a terminal end of the suture into a distal opening of a longitudinal bore extending through the suture anchor, and passing the terminal end of the suture through a substantially transverse bore formed in a body of the suture anchor such that the terminal end surface of the suture extends outside of the body of the suture anchor.

In some embodiments, a center of the substantially transverse bore can be located approximately 90 degrees around a circumference of an outer surface of the body of the suture anchor from a longitudinal axis extending between a proximal terminal end surface of the body and a distal end of the bore identification feature. Alternatively, a center of the substantially transverse bore can be located approximately along a longitudinal axis extending between a proximal terminal end surface of the body and a distal end of the bore identification feature. The bore identification feature can be integrally formed as part of an elongate cylindrical body of the suture anchor. In such embodiments, the elongate cylindrical body can have a first length extending between a proximal terminal end surface of the body and a distal terminal end surface of the body that is greater than a second length extending between the proximal terminal end surface and the distal terminal end surface, with the first and second lengths being measured along opposed sides of an outer surface of the elongate cylindrical body. Further, in some embodiments, the bore identification feature can include a cylindrical wedge extending from a distal terminal end surface that is substantially flat.

BRIEF DESCRIPTION OF DRAWINGS

FIG. 1A is a right side view of one exemplary embodiment of a suture anchor;

FIG. 1B is a left side view of the suture anchor of FIG. 1A;

FIG. 1E is a top side view of the suture anchor of FIG. 1A;

FIG. 1F is a bottom side view of the suture anchor of FIG. 1A;

DETAILED DESCRIPTION

Figure 1C:
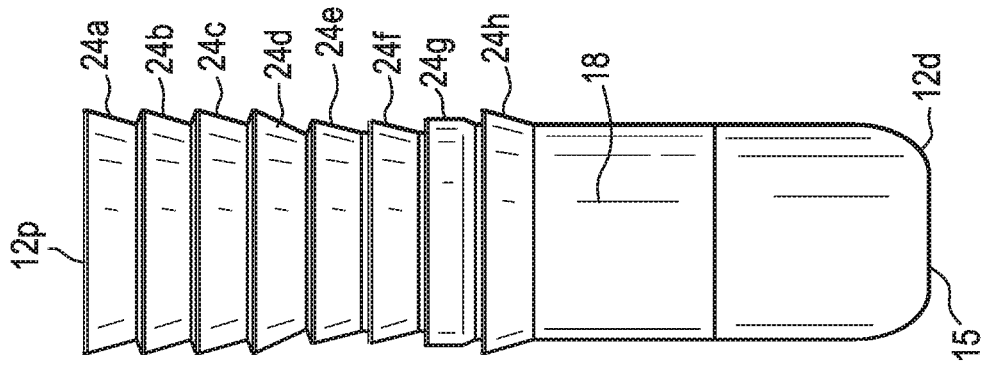
FIG. 1C is a rear side view of the suture anchor of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of the devices, and the components thereof, can depend at least on the anatomy of the subject in which the devices will be used, the size and shape of components with which the devices will be used, and the methods and procedures in which the devices will be used. The figures provided herein are not necessarily to scale. Additionally, a number of terms may be used throughout the disclosure interchangeably but will be understood by a person skilled in the art. By way of non-limiting example, the terms "suture" and "filament" may be used interchangeably.

Devices and methods are generally provided to assist a user in locating a bore into which a suture anchor is to be implanted. The devices include various enhanced constructions that include some form of an identification feature at a distal end of the device. The identification feature can be configured to quickly and easily detect the location of a bore, for instance by passing into the bore while a remaining portion of the anchor is not necessarily located in the bore. Once the bore has been located using the identification feature, the anchor can be implanted into the bore and a procedure performed, all while not tying any knots. In some tests, it has been found that bore identification has occurred in about eight seconds using devices as provided for herein, as opposed to the one minute or longer associated with prior art anchors during similar testing. The identification feature can include, by way of non-limiting examples, one side or length of an anchor being longer than a second, opposed side, and/or a protrusion, tooth, or key disposed on a portion of the distal end of the anchor. A person skilled in the art will recognize that the ability to quickly and easily identify a location of a bore into which an anchor is going to be implanted is useful in many different procedures, including but not limited to soft tissue repair procedures involving the glenoid, rotator cuff, and other types of tendon and tissue.

In one exemplary embodiment, as shown in FIGS. 1A-1E, a suture anchor 10 can include a generally cylindrical elongate body 12 that is sized and shaped to fit, and be fixed, into a corresponding bore made, or otherwise located, in a bone. The elongate body 12 extends from a proximal terminal end surface 12p to a distal terminal end surface 12d, and includes a lumen 14 extending between the two end surfaces 12p, 12d along a central longitudinal axis $C_A$. In alternative embodiments, the lumen 14 may not extend fully through a length of the body 12, and instead may extend from the distal terminal end surface 12d to a location distal of the proximal terminal end surface 12p. For example, the lumen can be defined as the portion extending between the distal terminal end surface 12d and the bore or opening 16. As shown, the distal terminal end surface 12d surrounds the lumen 14.

As shown best in FIGS. 1A and 1B, portions of the body 12 can have disparate lengths, leading to a bore identification feature. For example, a first portion 12a of an outer wall 18 of the elongate body 12 can have a first length $L_1$, and a second portion 12b of the outer wall 18 of the elongate body 12, which is directly opposed to the first portion 12a, can have a second length $L_2$, where $L_1$ and $L_2$ can be different values. As shown, both the first length $L_1$ and the second length $L_2$ extend from the proximal terminal end surface 12p to the distal terminal end surface 12d, and thus, in the illustrated embodiment, the proximal and distal terminal end surfaces 12p and 12d are not perpendicular across their lengths (their lengths being defined in FIGS. 1A and 1B as the distance extending between the first portion 12a of the outer wall 18 and the second portion 12b of the outer wall 18). In the illustrated embodiment, $L_1$ is larger than $L_2$ such that a distal portion 13 of the elongate body 12 forms a cylindrical wedge shape. While the lengths $L_1$ and $L_2$ can be any number of sizes, depending, at least in part, on the sizes and shapes of the other components with which the anchor is being used, the anatomy in which it is being implanted, and the type of procedure being performed, in some exemplary embodiments $L_1$ can be approximately in the range of about 9 millimeters to about 13 millimeters, and L2 can be approximately in the range of about 8 millimeters to about 10 millimeters, with a difference between L1 and L2 being approximately in the range of about 0.5 millimeters to about 3.0 millimeters. In the illustrated embodiment, the first and second portions 12a and 12b are on opposite sides from each other, but in other embodiments the two portions having disparate lengths to form a bore identification feature can be located at any location along the circumference of the elongate body 12.

An alternative manner for describing the disparate lengths associated with opposed sides of the elongate body 12 is to describe a first portion of the distal terminal end surface 12d, identified as portion F, projecting further away from the proximal terminal end surface 12p than a second portion of the distal terminal end surface 12d, identified as portion G, projects from the proximal terminal end surface 12p, with the first portion F being disposed on one side of the lumen 14 and the second portion G being disposed on a second, opposed side of the lumen 14. This configuration allows the first portion to be used to locate a bone hole for implantation of the suture anchor 10, as described in greater detail below.

In the illustrated embodiment, a distal most end 13d of the distal portion 13 along the first portion 12a forms a terminal identification surface or shoulder 15 that is substantially perpendicular to the central longitudinal axis $C_a$. The terminal identification surface 15, as a result of the disparate lengths of the first and second portions 12a and 12b, provides a surgeon the ability to receive more accurate tactile feedback to find a bone bore. Because the first length $L_1$ and the second length $L_2$ are of different values, the distal terminal end surface 12d is sloped between the first and second portions 12a and 12b. Alternatively, the distal terminal end surface 12d can have other, not necessarily sloped profiles, such as a profile that includes one or more curves, e.g., convex or concave curves. In the illustrated embodiment, the slope of the distal terminal end surface 12d can function as a ramp to guide the suture anchor 10 into a bore once the terminal identification surface 15 is disposed at least partially in a bore, as discussed below. The ramped distal terminal end 12d can additionally prevent entanglement of the suture around the distal portion 13 by causing the suture to slide down and off the distal portion 13 in the event the anchor 10 becomes rotated about the suture. As shown in FIGS. 1E and 1F, in some embodiments a thickness $T_1$ of the terminal identification surface 15 can be equal to or less than a thickness $T_2$ extending between an inner wall 20 and the outer wall 18 of the elongate body 12.

As shown in FIG. 1C, in some embodiments the distal terminal end surface can form a variety of thicknesses between the inner and outer walls 20 and 18. More particularly, a thickness can taper as the surface extends proximally such that a thickness $t_c$ at a central portion 12dc can be thicker than a thickness $t_p$ at a proximal portion 12dp.

As shown in FIG. 1B, the elongate body 12 can further include at least one suture bore or opening 16 extending from the outer surface 18 to the inner surface 20 of the elongate body 12. The suture bore 16 can be sized such that one or more suture tails 22a, 22b can be passed therethrough. In the illustrated embodiment, two suture tails 22a, 22b extend from a distal end of the lumen 14, proximate to the distal portion 13, through a portion of the lumen, and through the suture bore 16. The suture bore 16 can be located in a portion of the body 12 proximate to the proximal terminal end 12p of the elongate body 12. More particularly, in the illustrated embodiment the bore 16 is disposed proximal of the distal portion 13, and approximately centrally along the length $L_2$ of the second portion 12b. A person skilled in the art will recognize, however, that the suture bore 16 can be located any suitable distance proximate to the distal portion 13.

The suture bore 16 extends through the elongate body 12 at an angle that is offset from the central longitudinal axis $C_a$ of the elongate body 12. As shown it can include an outer lip 16a having a chamfered, beveled, or rounded configuration to provide a surface that is less likely to cause the suture tails 22a, 22b to tear, fray, or get caught against a surface defining the bore 16. As shown in FIG. 1B, the suture bore 16 is located approximately 90 degrees around a circumference of the outer surface 18 of the elongate body 12 from the terminal identification surface 15. This configuration can help prevent filament or suture tails disposed in the anchor 10 from becoming twisted, tangled, and/or fray, and can help make it easier to keep track of the filament disposed therein. In alternative embodiments, the suture bore 16 can be located at any location around the circumference of the elongate body 12. Still further, the suture bore 16 can be eliminated and the suture tails 22a, 22b, can be threaded through the lumen 14 of the elongate body from the proximal terminal end to the distal terminal end. In still further embodiments, the lumen 14 can extend from the suture bore 16 through the distal terminal end surface 12d, such that the proximal terminal end surface 12p does not have any portion of the lumen 14 extending therethrough. In the illustrated embodiment, the suture tails 22a, 22b are coupled to the anchor 10 by virtue of being passed through the lumen 14 and the bore 16, and engaging surfaces of the anchor 10 as a result. In some embodiments, one or more features can be incorporated as part of the anchor 10 to directly secure the suture tails 22a, 22b to the anchor 10. Such features are not necessary, however, in view of the fact that the tails 22a, 22b are typically used to grasp and draw tissue towards the anchor, and are thus prevented from becoming disassociated from the anchor 12 by virtue of their engagement with the tissue and/or with the respective tails 22a, 22b and/or with other components typically used in tissue repair procedures.

Figure 1D:
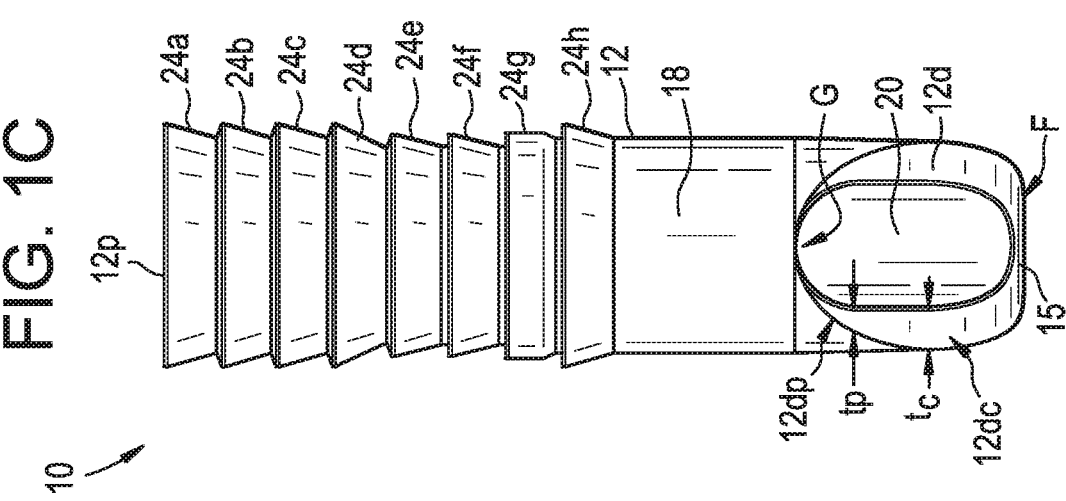
FIG. 1D is a front side view of the suture anchor of FIG. 1A.

Opposed sides of the outer surface 18 of the elongate body 12 can be tapered between the proximal end 12p and the distal end 12d. As shown, there is a slight taper in the body 12 such that a thickness at the proximal end 12p is greater than a thickness at the distal end 12d. Alternatively, opposed side of the outer surface 18 can be substantially parallel to the longitudinal axis $C_A$. The outer surface 18 of the elongate body 12 can include one or more bone engaging features, as shown ribs 24a, 24b, 24c, 24d, 24e, 24f, 24g, 24h, to secure the suture anchor 10, and thereby the suture tails 22a, 22b disposed therein, relative to the bone bore. In the illustrated embodiment, the bone engaging features 24a-24h are radially extending ribs which extend radially out of the outer surface 18. The earlier described taper can be a result of the shape of the ribs, or the taper can be independent of any use of ribs or other bone engaging features. As shown in FIGS. 1C and 1D, the ribs 24a-24h can be located on the outer surface 18 on an intermediate or proximal portion of the elongate body 12. The ribs 24a-24h can be sized to create an interference fit between the suture anchor 10 and the surface of the bone that defines a bore formed in the bone to retain the suture anchor 10 in the bone. In the illustrated embodiment there are eight ribs 24a-24h disposed along the elongate body 12, the ribs 24a-24h extending more than halfway down the second portion 12b, and approximately halfway down the first portion 12a. In alternative embodiments, the suture anchor 10 can include any number of bone engaging features extending any length of the body 12, including along the entire body 12. Other exemplary bone engaging features can include threads, a roughened, or a knurled surface. Further, it is contemplated that the suture anchor need not include any bone engaging features and instead could be fixed in the bore using other known techniques, including but not limited to an adhesive. Still further, an adhesive can be used in conjunction with any bone engaging feature, including the ribs 24a-24h.

While the illustrated embodiment provides for an elongate, generally cylindrical body 12, a person skilled in the art will recognize that the elongate body can take on any shape, for example, a cone, a triangular prism, a polyhedron of any number of sides, etc. Likewise, as described above with respect to the lengths L1 and L2, a size of the anchor 10, and components thereof, can depend on many different factors, and can be optimized to achieve different sizes for different anatomies. While some non-limiting ranges of lengths are provided above, it is worth noting some non-limiting ranges of diameters as well. Accordingly, in some embodiments, the elongate body 12 can have an outer diameter approximately in the range of about 2 millimeters to about 4 millimeters, and an inner diameter approximately in the range of about 1 millimeter to about 3 millimeters, with the outer diameter being defined by a distance between the opposed sides of the outer wall 18 and the inner diameter being defined by opposed side of the inner wall 20, i.e., the diameter of the lumen 14.

It will be appreciated by a person of skill in the art that the suture anchor 10 can be manufactured in any number of different pieces as would be required. By way of non-limiting example, as illustrated in FIGS. 1A-1D, the suture anchor 10 can be made of a uniform piece of material. The suture anchor 10 can be manufactured from any number of materials, including but not limited to bone, osteoinductive and osteoconductive composite materials, bio-resorbable and non-resorbable polymers, metal, and combinations thereof. In some embodiments the suture and/or the anchor can be impregnated with material to induce bone growth, or other medications to promote healing at the surgical site. In yet other embodiments, different portions of the suture anchor 10 can be manufactured from different materials then assembled together. For example, the distal portion 13, can be manufactured from titanium while the remaining portion can be made from plastic. Further, any edge of the suture anchor 10 can be chamfered, beveled, or rounded.

Figure 2:
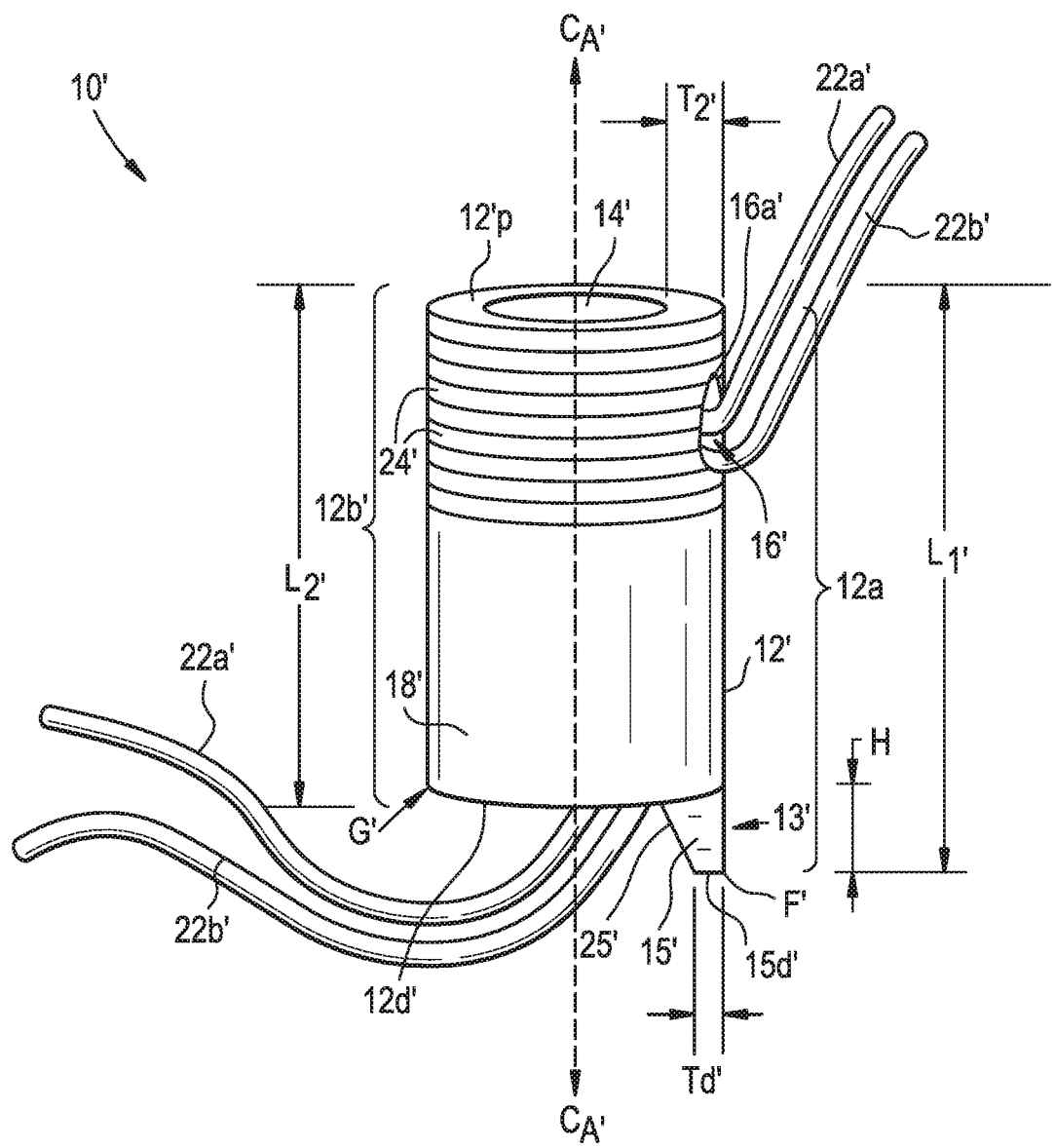
FIG. 2 is a schematic view of another exemplary embodiment of a suture anchor.

Another exemplary embodiment of a suture anchor 10' is illustrated in FIG. 2, with the anchor 10' having a distal portion 13' that is shaped differently than the distal portion 13 of the suture anchor 10. The suture anchor 10' generally can be of the same construction as the suture anchor 10, and thus includes a generally cylindrical elongate body 12' that extends from a proximal end 12p' to a distal end 12d' with a lumen 14' extending between the two ends 12p', 12d'. This second embodiment also includes two portions 12a', 12b' that have disparate lengths $L_1'$, $L_2'$, respectively, although the length $L_1'$ of the first portion 12a' is based on a length of the body 12' and a length of a protrusion 15', sometimes referred to as a tooth, key, cylindrical wedge, or bore identification feature, that extends from the distal end 12d' of the body 12'. The dimensions as described above with respect to $L_1$ and $L_2$ of the anchor 10 are similarly applicable to the anchor 10', although the dimensions with respect to both embodiments are not limiting. While the lengths $L_1'$, $L_2'$ are disparate, because the length $L_1'$ of the first portion 12a' includes both a length of the body 12' and a length of the protrusion 15', in the illustrated embodiment the length of the body 12' absent the protrusion 15' is actually approximately equal for opposed sides of the anchor 10'. As a result, but for the protrusion 15', the profile of the distal terminal end 12d' that extends between the two portions 12a', 12b' is substantially parallel to the surface that forms the proximal end 12p'. Similar to the anchor 10, in alternative embodiments the profile of the distal terminal end 12d' can have any geometric profile. Other similar features of the anchor 10' can include a tapered outer surface or wall 18', bone engaging features 24", e.g., radially extending ribs, formed on the outer surface 18' of the body 12', and a suture bore 16' extending from the outer surface 18' to an inner surface 20' such that the suture bore 16' is in working communication with the lumen 14' to allow one or more suture tails 22a', 22b' to pass distally from the suture bore 16' through the lumen 14'. In the illustrated embodiment, the suture bore 16' is substantially aligned with the protrusion 15' along the outer surface 18', although in other embodiments the suture bore 16' can be located along any portion of a circumference of the elongate body 12' as described above with respect to the anchor 10. In some embodiments, the suture bore 16' can extend through the elongate body 12" at an angle that is offset from the central longitudinal axis $C_a'$ of the elongate body 12', and an outer lip 16a' of the suture bore 16' can have a chamfered, beveled, or rounded configuration to provide a surface that is less likely to cause the suture tails 22a', 22b' to tear, fray, or get caught against a surface defining the bore 16'. As described above, in other embodiments, no bore 16' may be provided.

An alternative manner for describing the disparate lengths associated with opposed sides of the elongate body 12' is to describe a first portion of the distal terminal end surface 12d', identified as portion F', projecting further away from the proximal terminal end surface 12p' than a second portion of the distal terminal end surface 12d', identified as portion G', projects from the proximal terminal end surface 12p', with the first portion F' being disposed on one side of the lumen 14' and the second portion G' being disposed on a second, opposed side of the lumen 14'. This configuration allows the first portion to be used to locate a bone hole for implantation of the suture anchor 10', as described in greater detail below.

The bore identification feature 15' can have a variety of different configurations that make it conductive to being able to easily identify a location of a bore in a bone in view of the disclosures provided for herein. As shown, the bore identification feature 15' is substantially wedge-shaped and includes a flat distal most surface or shoulder 15d' having a thickness $T_d'$ that is less than a thickness $T_2'$ measured between the outer and inner surfaces 18', 20'. A height H of the bore identification feature can be approximately in the range of about 0.5 millimeters to about 3 millimeters, i.e., similar to a height of the difference between lengths $L_1$ and $L_2$ for the anchor 10. An inner surface 25' of the bore identification feature 15' can be tapered from the distal most surface 15d' to the distal terminal end surface 12d', thereby creating a ramped surface. The ramped inner surface 25' can additionally prevent entanglement of the suture 22a', 22b' around the bore identification feature 15' by causing the suture to slide down and off the bore identification feature 15' in the event the anchor 10' becomes rotated about the suture. The disclosures related to materials and manufacturing techniques for the anchor 10 are equally applicable to the anchor 10'. Further, the bore identification feature 15', can be integrally formed with the body 12', or it can be separately formed from the body 12'. In some instances, it may be adhered or coupled directly to an existing suture anchor. It can likewise be formed from the same or different materials as the rest of the anchor 10'.

In one exemplary embodiment of a surgical procedure utilizing the suture anchor 10', a surgeon or other user can initially drill a bore 30 in bone 40. Alternatively, the user can modify an existing bore, or identify a pre-existing bore, for use with the suture anchor 10'. If a drill guidewire was used in conjunction with bore formation, it can be removed. Once the bore 30 has been prepared, the suture tails 22a', 22b' can be threaded through the soft tissue according to accepted surgical techniques. Then the sutures 22a", 22b" are threaded through the suture anchor 10', for example by first going through the suture bore 16', then through the distal end of the lumen 14'. The suture tails 22a', 22b' can be threaded through the suture anchor 10' outside of the body, or inside of the body at the surgical site, depending, at least in part, on the type of procedure being performed and the preferences of the user. For example, although not illustrated, in some instances the suture may be positioned at the surgical site, even within the bore, prior to coupling or otherwise associating the suture with the anchor 10'.

Figure 3A:
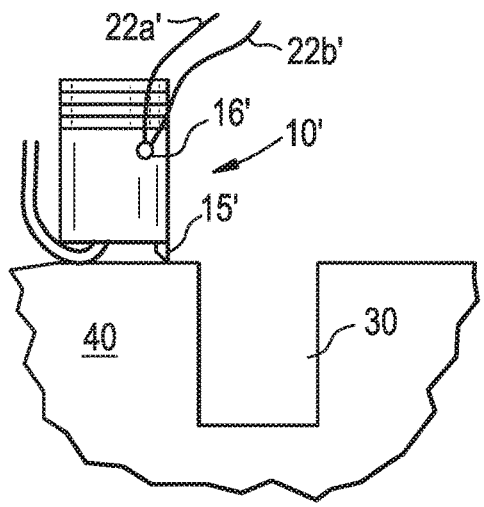
FIG. 3A-3E are sequential, schematic side views of one exemplary embodiment of a method for implanting the suture anchor of FIG. 2 into a bone tunnel.

The suture anchor 10' can be inserted to the surgical site, e.g., a bone of a patient, in accordance with customary surgical procedures, which can include open surgery or minimally invasive surgery (e.g., using one or more access cannulae). As shown in FIG. 3A, the body 12' and/or the bore identification feature 15' of the suture anchor 10' contacts the bone 40. Of note, because the bore identification feature 15' extends from the distal most end surface 12d' a distance greater than the diameter of the suture tails 22a', 22b', the suture tails 22a', 22b' are kept sufficiently out of the way to allow for the desired tactile feel of the surface 15d' contacting the bone. If desired, the suture tails 22a', 22b' can be pulled taught before the surgeon attempts to find the bore 30.

Figure 3B:
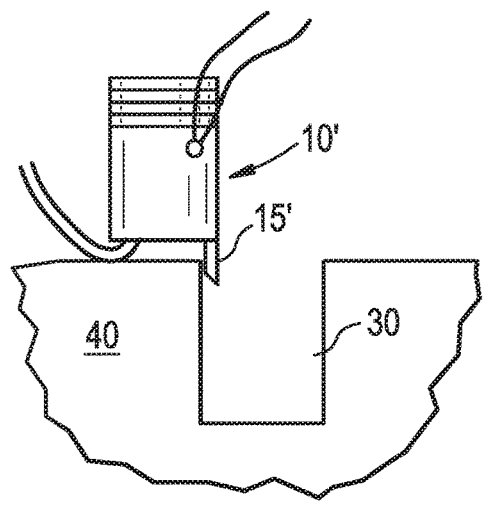
Figure 3C:
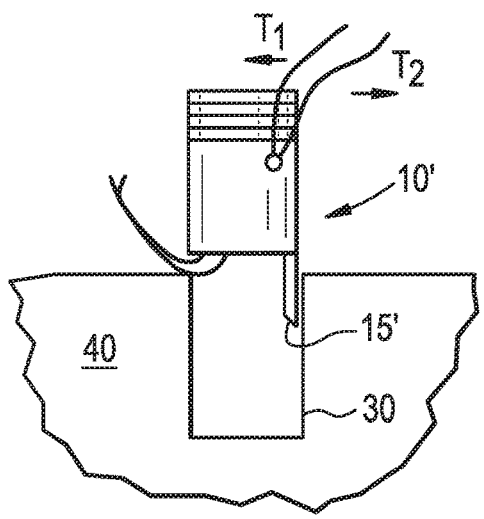
Figure 3D:
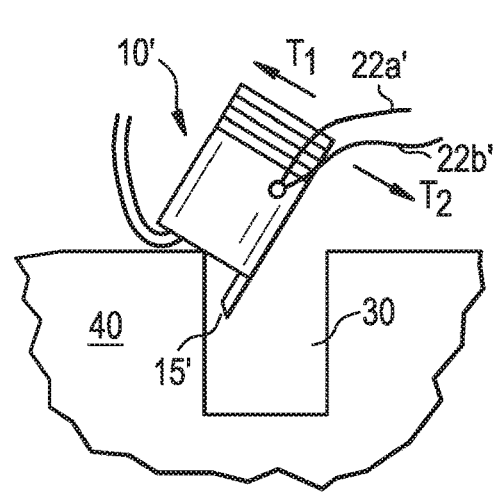
Figure 3E:
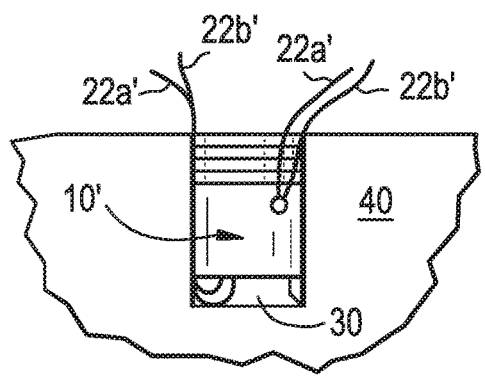

The suture anchor 10' can be moved along the bone 40 until the bore identification feature 15' drops into the bore 30, as shown in FIG. 3B. The suture anchor 10' provides for the added benefit of allowing the suture tails 22a', 22b' to be tightened without necessitating pulling the suture anchor 10' out of the bore 30 once the bore 30 has been found. The suture tails 22a', 22b' can be used to jostle the suture anchor 10', as shown by arrows $T_1$ and $T_2$, while the bore identification feature 15' is in the bore 30 such that the suture anchor 10' can then be fully inserted into the bore 30, as seen in FIGS. 3C and 3D. Once the bore 30 has been properly located by the operator with the bore identification feature 15', the suture anchor 10' can be fully installed into the bore 30. Full insertion of the suture anchor 10', as shown in FIG. 3E, can be achieved by the operator manually pushing or by the use of instruments such as a mallet or driver to advance the suture anchor 10' distally into the bore.

While this process is described with particular reference to suture anchor 10', one of ordinary skill will understand that the process is substantially the same when using the suture anchor 10. The bore identification feature 15 can drop into a bore once located, and the anchor 10 can be subsequently installed. This process greatly decreases the time required to complete the procedure, in some tests lowering the time from over one minute to identify a bore when no guidewire was present to approximately eight seconds. As multiple anchors are traditionally used in many procedures, this time savings is multiplied by each suture anchor of the present disclosure used.

This suture anchor system can be used, for example, in exemplary surgical procedures with respect to the glenoid fixation as described in U.S. patent application Ser. No. 14/339,577 of Bouduban et al., entitled "Systems, Devices and Methods for Guiding Surgical Devices into Bone," filed Jul. 24, 2014, the content of which is incorporated by reference in its entirety. A person skilled in the art will appreciate that the present invention has application in conventional minimally-invasive and open surgical instrumentation as well application in robotic-assisted surgery. Moreover, one of ordinary skill will appreciate that the bore identification features disclosed herein can be incorporating into many types of anchors and used in a variety of different procedures.

One skilled in the art will appreciate further features and advantages of the invention based on the above-described embodiments. Accordingly, the invention is not to be limited by what has been particularly shown and described, except as indicated by the appended claims. For example, to the extent the disclosures provided for herein describe devices and methods used in conjunction with glenoid labrum repairs, a person having skill in the art would be able to apply these disclosures to surgical procedures performed with other soft tissue repairs, and with other anatomies and in other locations of the body without departing from the spirit of the present disclosure. Further, although the devices and methods provided for herein are generally directed to surgical techniques, at least some of the devices and methods can be used in applications outside of the surgical field.

What is claimed is:

1. A surgical method of affixing tissue to bone, comprising:
   passing a suture through tissue;
   coupling the suture to a suture anchor, the suture anchor having a body with a proximal end opposed to a distal end and an outer surface defining a sidewall of the suture anchor, the distal end having a lumen through which the suture passes, and the body further having a first elongated portion that extends from the proximal end to the distal end to define a first length of the body and a second elongated portion that extends from the proximal end to the distal end to define a second length of the body, the first and second elongated portions being opposed sides of the outer surface of the body, the first length being greater than the second length such that the first elongated portion forms a bore identification feature of the suture anchor, the bore identification feature having a distal terminal end, the distal terminal end of the bore identification feature also being a distal terminal end of the suture anchor;
contacting an outer surface of a bone with the bore identification feature at a distance away from a location at which a bore is formed in the bone such that contacting the outer surface of the bone does not entail contacting a sidewall of the bore;
manipulating the suture anchor to position the suture anchor in the bore;
securing the suture anchor within the bore; and
manipulating the suture to secure a location of the tissue with respect to the bone.

2. The surgical method of claim 1, wherein the suture anchor is brought towards and positioned in the bore formed in the bone without assistance from at least one of a k-wire or guide wire.

3. The surgical method of claim 1, further comprising drilling the bore formed in the bone.

4. The surgical method of claim 1, wherein manipulating the suture anchor to position the suture anchor in the bore further comprises applying tension to the suture.

5. The surgical method of claim 1, wherein coupling the suture to the suture anchor further comprises:
passing a terminal end of the suture into a distal opening of the lumen extending through the suture anchor; and
passing the terminal end of the suture through a substantially transverse bore formed in a body of the suture anchor such that a terminal end surface of the suture extends outside of the body of the suture anchor.

6. The surgical method of claim 5, wherein a center of the substantially transverse bore is located approximately 90 degrees around a circumference of the outer wall of the body of the suture anchor from a longitudinal axis that extends through both of a proximal terminal end surface of the body and a distal-most surface of the bore identification feature.

7. The surgical method of claim 5, wherein a center of the substantially transverse bore is located approximately along a longitudinal axis extending between a proximal terminal end surface of the body and a distal end of the bore identification feature.

8. The surgical method of claim 1, wherein the bore identification feature is integrally formed as part of an elongate cylindrical body of the suture anchor.

9. The surgical method of claim 1, wherein the bore identification feature comprises a cylindrical wedge.

10. The surgical method of claim 1, wherein the bone anchor is a unitary piece.

11. The method of claim 1,
wherein the sidewall has one or more bone engaging features configured to engage and secure the suture anchor to a wall of a bore formed in a bone, and
wherein securing the suture anchor within the bore occurs by the one or more bone engaging features engaging a sidewall of the bore formed in the bone.

12. A surgical method of affixing tissue to bone, comprising:
passing a suture through tissue;
coupling the suture to a suture anchor, the suture anchor having a body defined by an outer wall extending between a proximal terminal end and a distal terminal end, and a bore identification feature associated with the distal terminal end;
moving the suture anchor substantially laterally along and in contact with a surface of a bone that has a bore disposed therein with a central longitudinal bore axis extending through a length of the bore such that the suture anchor is in contact with the surface of the bone as it is being moved substantially laterally relative to the longitudinal bore axis to cause the bore identification feature to enter the bore;
manipulating the suture anchor to position the suture anchor in the bore;
securing the suture anchor within the bore; and
manipulating the suture to secure a location of the tissue with respect to the bone.

13. The method of claim 12, wherein the suture anchor is moved along the surface of the bone such that a central longitudinal axis that extends through the body from the proximal terminal end to the distal terminal end is substantially perpendicular to the surface of the bone.

14. The method of claim 13, wherein the bore identification feature enters the bore prior to the outer wall of the suture anchor being aligned with the bore for entry into the bore.

15. The method of claim 14, wherein the bore identification feature is disposed radially outward from the central longitudinal axis such that the bore identification feature is at a periphery of the suture anchor.

16. The method of claim 12, wherein the bone anchor is a unitary piece.

17. A surgical method of affixing tissue to bone, comprising:
passing a suture through tissue;
coupling the suture to a suture anchor, the suture anchor having a body with a proximal-most point and a distal-most point along a first axis of the suture anchor, and a proximal-most point and a distal-most point along a second axis of the suture anchor, the first and second axes being on diametrically opposed sides of an outer surface of the suture anchor, the body having a first elongated portion that extends from the proximal-most point on the first axis to the distal-most point on the first axis to define a first length of the body that is a longest length of the body, and a second elongated portion that extends from the proximal-most point on the second axis to the distal-most point on the second axis to define a second length of the body, the body having a first plane that extends through the first and second elongated portions, the first length being greater than the second length such that the first elongated portion forms a bore identification feature of the suture anchor, and a distal end of the body defining an annular surface, the distal end tapering from the distal-most point on the first axis, and thus the bore identification feature, to the distal-most point on the second axis across a second plane centrally located between the first and second elongated portions and substantially perpendicular to the first plane;
identifying, using the bore identification feature, a bore formed in a bone without at least one of a k-wire or a guide wire to align the anchor with respect to the bore;
manipulating the suture anchor to position the suture anchor in the bore;
securing the suture anchor within the bore; and
manipulating the suture to secure a location of the tissue with respect to the bone.

18. The method of claim 17, wherein coupling the suture to the suture anchor further comprises passing a terminal end of the suture into a distal opening of a longitudinal bore, the longitudinal bore extending through the suture anchor, from a proximal end to a distal end of the body.

19. The method of claim 17, further comprising moving the suture anchor along a surface of the bone having the bore disposed therein to cause the bore identification feature to enter the bore.

20. The surgical method of claim 17, wherein a center of a substantially transverse bore formed in the body of the suture anchor is located approximately 90 degrees around a circumference of an outer surface of the body of the suture anchor from the first axis.

21. The method of claim 17, wherein the bone anchor is a unitary piece.

22. A surgical method of affixing tissue to bone, comprising:

passing a suture through tissue;

coupling the suture to a suture anchor, the suture anchor having an elongate cylindrical body including an outer wall and a bore identification feature, the outer wall having a first length that extends between a proximal terminal end surface of the body and a distal terminal end surface of the body and a second length that extends between the proximal terminal end surface of the body and the distal terminal end surface of the body, the first and second lengths being measured along opposed sides of the outer wall with the first length being greater than the second length, the bore identification feature being at least part of the distal terminal end surface that extends between the first and second lengths, and the anchor further including a longitudinal bore extending through the suture anchor, from the proximal terminal end surface to the distal terminal end surface, the longitudinal bore having a distal opening at the distal terminal end surface, wherein coupling the suture to the suture anchor includes passing a terminal end of the suture into the distal opening;

contacting an outer surface of a bone with the bore identification feature at a distance away from a location at which a bore is formed in the bone such that contacting the outer surface of the bone does not entail contacting a sidewall of the bore, and manipulating the suture anchor to position the suture anchor in the bore, thereby providing tactile feedback to distinguish between when the bore identification feature contacts a portion of the outer surface of the bone distinct from any surface of the bone that defines the bore and when the bore identification feature enters the bore formed in the bone;

securing the suture anchor within the bore; and manipulating the suture to secure a location of the tissue with respect to the bone.

23. The method of claim 22, further comprising moving the suture anchor along a surface of the bone having the bore disposed therein to cause the bore identification feature to enter the bore.

24. The method of claim 22, wherein a center of a substantially transverse bore formed in the elongate cylindrical body of the suture anchor is located approximately 90 degrees around a circumference of the outer wall of the body of the suture anchor from a longitudinal axis that extends through both of the proximal terminal end surface and a distal-most surface of the bore identification feature.

25. The method of claim 22, wherein the bone anchor is a unitary piece.

* * * * *